(12) United States Patent
Gabbay (10) Patent No.: US 7,510,573 B2
(45) Date of Patent: Mar. 31, 2009

(54) SIZING APPARATUS

(76) Inventor: Shlomo Gabbay, 112 W. 56th St., Apt. 9N, New York, NY (US) 10019

( * ) Notice: Subject to any disclaimer, the term of this patent is extended or adjusted under 35 U.S.C. 154(b) by 233 days.

(21) Appl. No.: 11/214,104

(22) Filed: Aug. 29, 2005

(65) Prior Publication Data

US 2005/0283232 A1 Dec. 22, 2005

Related U.S. Application Data (60) Continuation-in-part of application No. 11/132,059, filed on May 18, 2005, which is a division of application No. 10/396,656, filed on Mar. 25, 2003, now abandoned.

(51) Int. Cl.
*A61F 2/24* (2006.01)
(52) U.S. Cl. .................................... 623/2.11
(58) Field of Classification Search .......... 623/2.1–2.11
See application file for complete search history.

(56) References Cited

U.S. PATENT DOCUMENTS

| | | | |
|---|---|---|---|
| 1,488,463 A | 4/1924 | Edmund | |
| 1,767,659 A | 6/1930 | Ferguson | |
| 4,042,979 A | 8/1977 | Angell | |
| 4,240,161 A | 12/1980 | Huffstutler et al. | |
| 4,350,492 A | 9/1982 | Wright et al. | |
| 4,491,986 A | 1/1985 | Gabbay | |
| 4,759,758 A | 7/1988 | Gabbay | |
| 5,258,021 A | 11/1993 | Duran | |
| 5,549,665 A | 8/1996 | Vesely et al. | |
| 5,584,879 A | 12/1996 | Reimold et al. | |
| 5,800,527 A | 9/1998 | Jansen et al. | |
| 5,861,028 A | 1/1999 | Angell | |
| 6,092,523 A * | 7/2000 | Belfer ......................... | 128/848 |
| 6,110,200 A | 8/2000 | Hinnenkamp | |
| 6,129,758 A | 10/2000 | Love | |
| 6,350,281 B1 | 2/2002 | Rhee | |
| 6,419,695 B1 | 7/2002 | Gabbay | |
| 6,517,576 B2 | 2/2003 | Gabbay | |
| 6,598,307 B2 | 7/2003 | Love et al. | |
| 6,613,085 B1 * | 9/2003 | Anderson et al. .......... | 623/2.11 |
| 6,719,785 B2 | 4/2004 | Schoon | |
| 6,869,444 B2 | 3/2005 | Gabbay | |
| 2002/0103531 A1 | 8/2002 | Stobie | |
| 2003/0069586 A1 * | 4/2003 | Errico et al. .................. | 606/99 |
| 2003/0078651 A1 | 4/2003 | Schoon et al. | |
| 2004/0059413 A1 * | 3/2004 | Argento ..................... | 623/2.11 |
| 2008/0097593 A1 * | 4/2008 | Bolling et al. ............. | 623/2.36 |

FOREIGN PATENT DOCUMENTS

DE 197 45 847 C1 7/1997
DE 19745847 * 10/1997

* cited by examiner

*Primary Examiner*—Suzette J Gherbi
(74) *Attorney, Agent, or Firm*—Tarolli, Sundheim, Covell & Tummino LLP (57) ABSTRACT

A sizing apparatus can include a contact member having a curved contact surface, the contact surface extending in a substantially convex shape from a proximal end to a distal end along a direction that lies in a same plane as a first axis, the contact surface extending in a substantially concave shape between spaced apart first and second side edges along a direction that lies in a plane that is substantially transverse to the first axis. The sizing apparatus can also include an arm extending from the contact member substantially parallel to the first axis. A flange may also be provided to facilitate use of the sizing apparatus.

8 Claims, 7 Drawing Sheets

SIZING APPARATUS

CROSS-REFERENCE TO RELATED APPLICATIONS

This application is a continuation-in-part of application Ser. No. 11/132,059, which was filed May 18, 2005, and entitled "METHOD OF DETERMINING SIZE OF CARDIAC PROSTHESIS", which is a divisional of application Ser. No. 10/396,656, which was filed Mar. 25, 2003 now abandoned, and entitled "SIZING APPARATUS FOR CARDIAC PROSTHESIS AND METHOD OF USING SAME" both of which are incorporated herein by reference.

TECHNICAL FIELD

The present invention relates generally to cardiac prostheses and, more particularly, to a sizing apparatus such as for a cardiac prosthesis.

BACKGROUND

A heart valve can become defective or damaged, such as resulting from congenital malformation, disease, or aging. When the valve becomes defective or damaged, the leaflets may not function properly. One common problem associated with a degenerating heart valve is an enlargement of the valve annulus (e.g., dilation). Other problems that may result in valve dysfunction are chordal elongation and lesions developing on one or more of the leaflets.

The bicuspid or mitral valve is located in the left atrioventricular opening of the heart for passing blood unidirectionally from the left atrium to the left ventricle of the heart. The mitral valve is encircled by a dense fibrous annular ring and includes two valve leaflets of unequal size. A larger valve leaflet, which is known as the anterior leaflet, is located adjacent the aortic opening. The smaller leaflet is the posterior leaflet.

When a mitral valve functions properly, for example, it prevents regurgitation of blood from the ventricle into the atrium when the ventricle contracts. In order to withstand the substantial backpressure and prevent regurgitation of blood into the atrium during the ventricular contraction, the cusps are held in place by fibrous cords (cordae tendinae) that anchor the valve cusps to the muscular wall of the heart.

By way of example, if an annulus enlarges or dilates to a point where the attached leaflets are unable to fully close (malcoaptation), regurgitation or valve prolapse might occur. Adverse clinical symptoms, such as chest pain, cardiac arrhythmias, dyspnea, may manifest in response to valve prolapse or regurgitation. As a result, surgical correction, either by valve repair procedures or by valve replacement, may be required.

Surgical reconstruction or repair procedures may include plication, chordal shortening, or chordal replacement. Another common repair procedure relates to remodeling of the valve annulus (e.g., annuloplasty), which may be accomplished by implantation of a prosthetic ring to help stabilize the annulus and to correct or help prevent valvular insufficiency which may result from defect or dysfunction of the valve annulus. Properly sizing and implanting the annuloplasty ring can substantially restore the valve annulus restored to its normal, undilated, circumference. In situations where the valve leaflets exhibit lesions, it also may be necessary to reconstruct one or more valve leaflets by securing grafts or patches to the leaflets, such as over lesions or holes formed in the leaflet. The repair or reconstruction of the leaflets may be complicated and time consuming, the results of which are not readily reproducible.

SUMMARY

The present invention relates generally to a sizer apparatus, such as for use in sizing a cardiac prosthesis or evaluating operation or a heart valve.

One aspect of the present invention provides a sizer apparatus that includes a contact member having a curved contact surface. The contact surface extends in a substantially convex shape from a proximal end to a distal end along a direction that lies in a same plane as a first axis. The contact surface extends in a substantially concave shape between spaced apart first and second side edges along a direction that lies in a plane that is substantially transverse to the first axis. An arm extends from the contact member substantially parallel to the first axis.

Another aspect of the present invention provides a sizing apparatus that includes a contact member having a curved contact surface. The contact surface extends in a substantially convex cross-sectional shape from a proximal end to a distal end along a first direction that lies in the same plane as a first axis. The contact surface extends in a substantially concave cross-sectional shape between spaced apart first and second side edges along a second direction that lies in a plane that is substantially transverse to the first direction. A flange extends outwardly from at least a portion of the proximal end of the contact member to define a shoulder along a surface of the flange that is opposite the contact surface of the contact member.

Yet another aspect of the present invention provides a sizing apparatus that includes a curved surface having an inflow end spaced apart from a distal end by spaced apart side edges that extend between the inflow end and the distal end, the curved surface being dimensioned and configured to simulate the dimensions and configuration of a coaptating surface of a heart valve leaflet at systole in closed position. A flange extends outwardly from at least a portion of the inflow end of the curved surface. An arm extends from the curved surface at a location that is proximal the inflow end of the curved surface.

DESCRIPTION

The present invention relates generally to a sizing apparatus for a cardiac prosthesis. The sizing apparatus can be used to determine the appropriate size for a cardiac prosthesis (e.g., a valvuloplasty device) that can be implanted into the heart valve to cooperate with at least one of the leaflets of the patient's own valve, which can be the patient's native valve or a previously implanted prosthesis. The sizing apparatus can also be utilized in other heart valve diagnosis and repair methods based on observations made while using the sizing apparatus.

Figure 1:
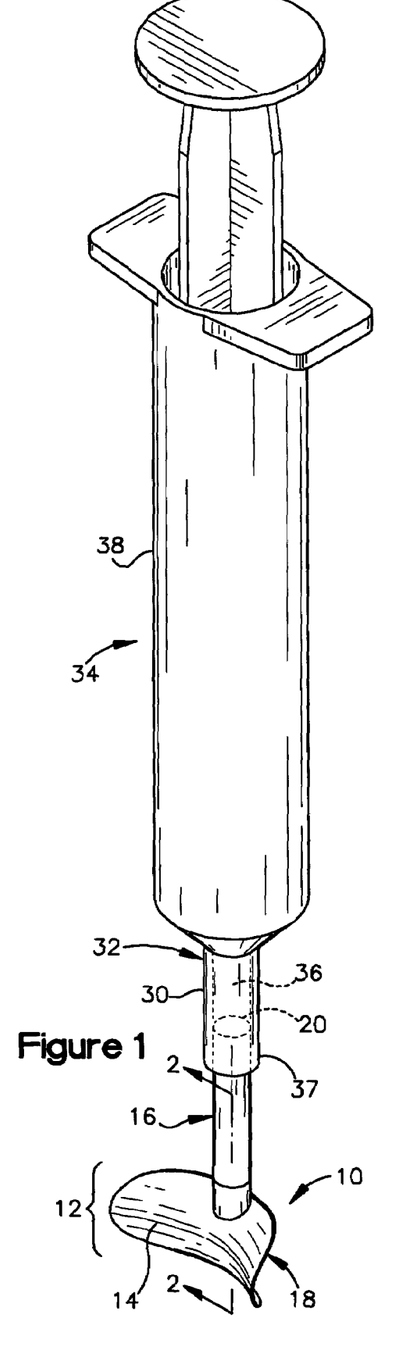
FIG. 1 is an elevated side view of an example apparatus in accordance with an aspect of the present invention.
Figure 2:
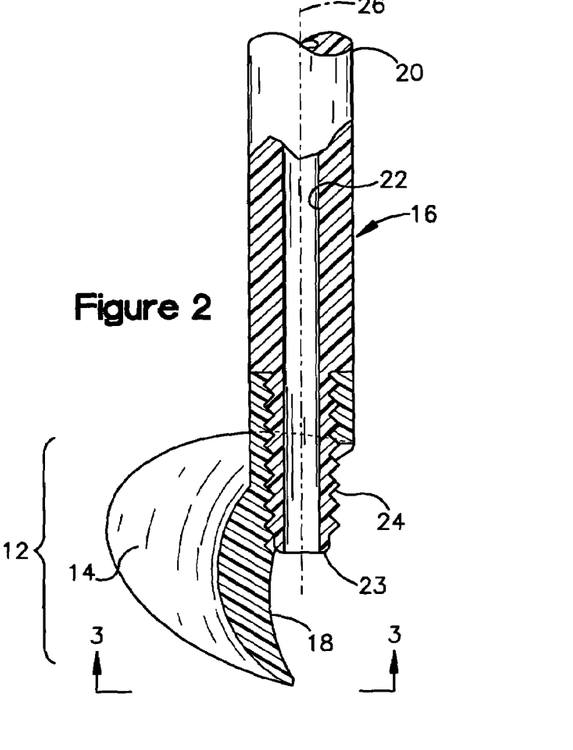
FIG. 2 is a cross-sectional view of the taken along line 2-2 of FIG. 1.
Figure 3:
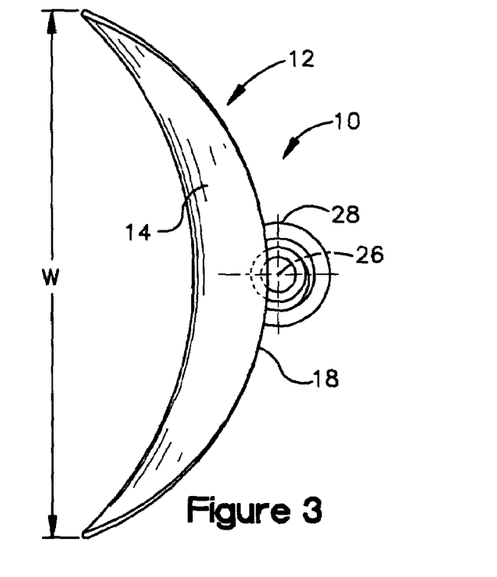
FIG. 3 is a view of the apparatus taken along line 3-3 of FIG. 2.

FIGS. 1-3 illustrate a sizer apparatus 10 in accordance with one aspect of the invention. The apparatus 10 includes a contact member 12. The contact member 12 has a curved surface 14 dimensioned and configured to be engaged by a leaflet within a heart valve. For example, the curved surface 14 can be configured to engage the anterior leaflet of the mitral valve of a patient's heart, such as by simulating a coaptating surface of the posterior (or another) leaflet in a closed position. As shown in FIGS. 1-3, the curved surface 14 extends in a substantially convex shape from a proximal end to a distal end along a direction that lies in a same plane as a longitudinal axis 26. The contact surface also extends in a substantially concave shape between spaced apart first and second side edges along a direction that lies in a plane that is substantially transverse to the axis 26.

In accordance with the present aspect of the invention, the contact member 12 can be fabricated from any substantially rigid, durable material that is substantially biocompatible. By substantially rigid, it is meant that the contact member 12 should be capable of holding its basic shape under a moderate amount of pressure. By durable, it is meant that the device should be able to withstand standard sterilization techniques, such as by an autoclave or other sterilizer. Example materials that can be used for the contact member include durable plastics (e.g., formed of DELRIN®) and non-reactive metals, such as surgical steel. Those skilled in the art will understand and appreciate other types of materials that also could be employed to form the contact member, all of which are contemplated as falling within the scope of the present invention.

An elongated member (or arm) 16 extends from the contact member 12 to terminate in a proximal end 20 that is spaced apart from the contact member. In the example of FIGS. 1-3, the elongated member is depicted as a generally cylindrical, elongated rod or tube, which can be hollow. As shown in FIG. 2, an aperture 22 extends through the elongated member 16 from its proximal end 20 to an opening located near a surface 18 of the contact member 12 opposite the surface 14.

The elongated member 16 can be formed of a durable and generally rigid material. The elongated member 16 can be formed of the same or a different material than the contact member 12. The length and composition of the elongated member 16 can vary, depending on the application. For example, some applications can require a lengthy elongated member 16 or an elongated member formed form a more flexible material. Those skilled in the art will appreciate that different materials and lengths can be selected depending on the design of the device and the desired application.

The elongated member 16 can also be formed of multiple portions, which can be the same or different materials. For example, the elongated member illustrated in FIG. 2 begins at its proximal end 20 as a plastic material. The inside of that portion of elongated member can be threaded (or otherwise configured) to accept a spout 24, which can be made from stainless steel, plastic (or any other generally rigid material) that terminates near the contact member 12. Alternatively, the contact member 12 can be formed from a single material, such as a metal or plastic material.

The contact member 12 is dimensioned to a size consistent with that of a leaflet within a heart valve. For example, a contact member 12 approximating the size of a leaflet within an adult human mitral valve can have a width (indicated at W in FIG. 3) ranging from fifteen to fifty millimeters. Those skilled in the art will appreciate that the width of the contact member can vary according to the application. For example, in a heart valve sizer apparatus intended for use in children or small animals, a width smaller than fifteen millimeters may be appropriate. An apparatus intended for use in large animals, such as horses, might require a contact member with a width greater than fifty millimeters.

As shown in FIG. 2, a longitudinal axis 26 extends longitudinally through the elongated member 16 substantially parallel to the aperture 22. While the member 16 is depicted as being substantially straight, it will be appreciated that it alternatively could be curved or formed a flexible material to facilitate curving the member. The contact surface 14 is curved in a convex manner relative to the axis 26. Another axis 28, shown in FIG. 3, is substantially perpendicular to the axis 26 and coincides with the longest dimension (e.g., the width W) of the contact member 12. The contact surface 14 is curved relative to the horizontal axis 28 in a concave manner (e.g., curves away). As a result of this curvature, the contact member 12 is configured to approximate a leaflet of a heart valve at closure of the valve.

The proximal end 20 of the elongated member 16 can connect to a sleeve-like conduit interface 30, as depicted in FIG. 1. The conduit interface 30 can be made from any durable, flexible material that is substantially biocompatible. Example materials include rubber or silicon, although other types of materials can also be used. The proximal end 32 of the conduit interface 30 is adapted to connect to a fluid source 34, which can include a syringe or other type of device capable of injecting fluid through the aperture 22. This adaptation allows the conduit interface 30 to fit tightly over a nozzle 36 of the fluid source 34, while the other end 37 of the conduit interface connects to the proximal end 20 of the elongated member 16. The conduit interface 30 thus can interconnect the elongated member 16 and the nozzle 36 to provide a substantially fluid-tight seal to enable the flow of fluids therethrough.

The fluid source 34 contains a quantity of a fluid that can be passed through the aperture 22 of the elongated member 16. A number of fluids can be used, including air, water, saline, and blood to name a few. In the illustrated apparatus, the fluid source includes a syringe 38. The syringe 38 can be used to expel fluid from the fluid source 34 through the nozzle 36 and into the aperture 22 of the elongated member 16. One skilled the art will perceive other devices for controlling the flow of fluid from the fluid source, such as stop cocks and mechanical or electric pumps, and the use of these devices is intended to be encompassed within the claimed invention. The fluid source 34 can be formed from a number of materials. For example, transparent materials, such as clear plastics and glass, can be used, as they allow a user to determine more easily the fluid level within the fluid source 34.

In view of various structural features of a sizer apparatus, in accordance with an aspect of the invention, use of such an apparatus to facilitate implantation of cardiac prosthesis will be better appreciated with reference to FIGS. 4-12. For example, as illustrated in FIGS. 4-7, implantation of a prosthesis can include the use of a sizing tool (or sizer apparatus) 52 to ascertain an appropriate size for a prosthetic device in accordance with an aspect of the present invention.

Figure 4:
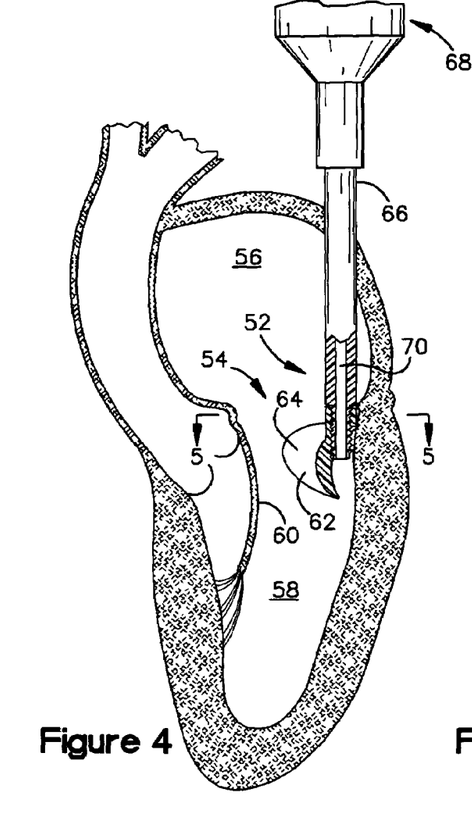
FIG. 4 is a cross-sectional view of the apparatus positioned within the heart valve of a patient, illustrating a first condition of the heart valve.

In FIG. 4, the sizing tool 52 has been inserted into a heart valve 54. Solely for the purpose of example, the valve 54 is illustrated in FIGS. 4-12 as a mitral valve within a human heart, and the method is discussed in the context of implanting a prosthesis to replace the posterior leaflet within the mitral valve. One skilled in the art will appreciate, however, that the apparatus of the present invention may be used in other valves within the human heart, such as the tricuspid, pulmonary, or aortic valves, as well as in valves within animal hearts. Likewise, the present invention may be used to size a replacement for any leaflet, including the anterior leaflet of the mitral valve or the leaflets of any of the aforementioned valves. Such uses are intended to be encompassed in the appended claims.

Figure 5:
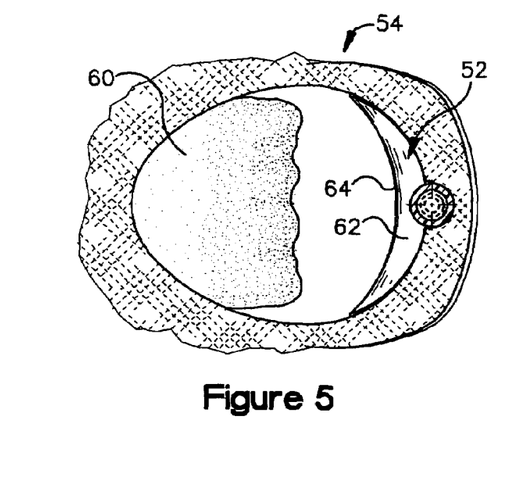
FIG. 5 is an overhead (inflow) view of the apparatus positioned within the heart valve of a patient, illustrating a first condition of the heart valve.

The chamber above the mitral valve 54 is the left atrium 56 and the chamber below the valve is the left ventricle 58. In FIG. 4, the anterior leaflet 60 is present and viable, but the posterior leaflet (not shown) is either non-viable or has been removed. A contact member 62 of the sizing tool 52 is positioned at the position formerly occupied by the posterior leaflet, with a contact surface 64 facing the anterior leaflet 60. In accordance with one aspect of the present invention, the contact member 62 can be positioned manually by a user holding an elongated handle 66 or other structure attached to the member. An inflow view of the open valve 54 and sizing apparatus 52 is shown in FIG. 5.

Figure 6:
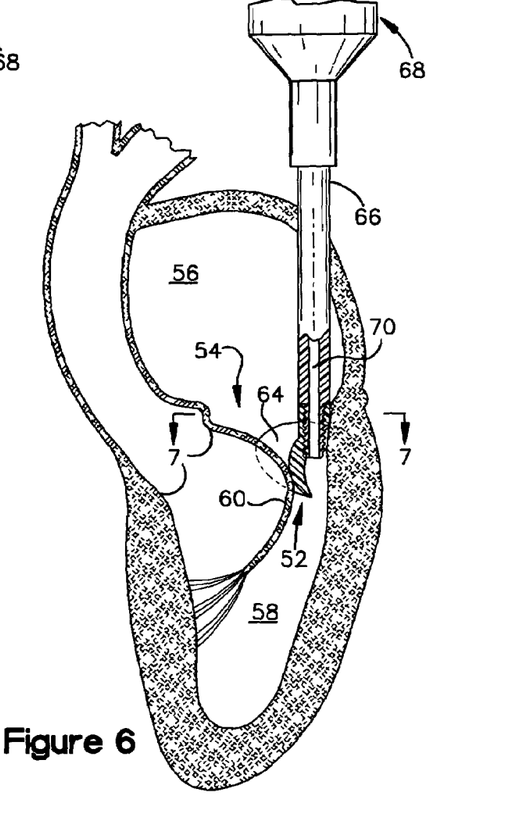
FIG. 6 is a cross-sectional view of the apparatus positioned within the heart valve of a patient, similar to FIG. 4, illustrating a second condition of the heart valve.

The user would employ a fluid source 68 in fluid communication with the apparatus 52 to supply fluid into the ventricle 58. Such fluid thus flows through an aperture 70 within the elongated handle 66 into the left ventricle 58. As discussed previously, this can be accomplished by a number of methods, such as a pump, syringe, or a stopcock. As the left ventricle fills 58 with fluid, the anterior leaflet 60 is urged toward its closed position and toward the contact member 62. Depending on whether the apparatus 52 is an appropriate size, the anterior leaflet 60 can engage with the contact member 62 to close the valve, as illustrated in FIG. 6.

Figure 7:
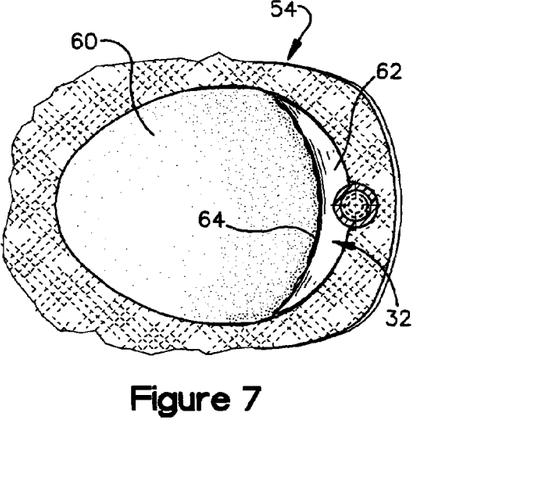
FIG. 7 is an overhead (inflow) view of the heart valve and the apparatus, similar to FIG. 5, illustrating a second condition of the heart valve.

Once the anterior leaflet 60 has been urged into a closed position, the surgeon can examine the engagement between the anterior leaflet and the contact member 62. Where the leaflet 60 and the contact member 62 coapt, as to substantially prevent the flow of fluid through from the valve, a size of a corresponding prosthesis can be determined according to the size of the contact member 62. An inflow view of a leaflet 60 coapting with a contact member 62 is illustrated in FIG. 7. When the leaflet 60 and the contact member 62 coapt properly, the surgeon will know that a prosthetic device matching the size and shape of the contact member 62 is appropriate for a prosthetic replacement. Where there is not sufficient coaptation between the leaflet 60 and the contact member 62, a differently sized prosthesis should be used.

For example, where the contact member 62 is too small to effectively coapt the leaflet 60, the surgeon may see small spaces or gaps between the leaflet and the contact member. This indicates a larger size prosthesis may be needed. This can be confirmed by repeating the sizing process with a larger sized contact member.

Where the contact member 62 is too large, the annulus of the valve 54 may distort, thereby preventing desired coaptation between the contact member 62 and the leaflet. Additionally or alternatively, the orifice between the contact member 62 and the leaflet may be considered be too small. A surgeon thus can readily ascertain that a prosthetic device matching the size of the contact member would be too large and seek a smaller device.

Figures 8, 9, 10, 11, 12:
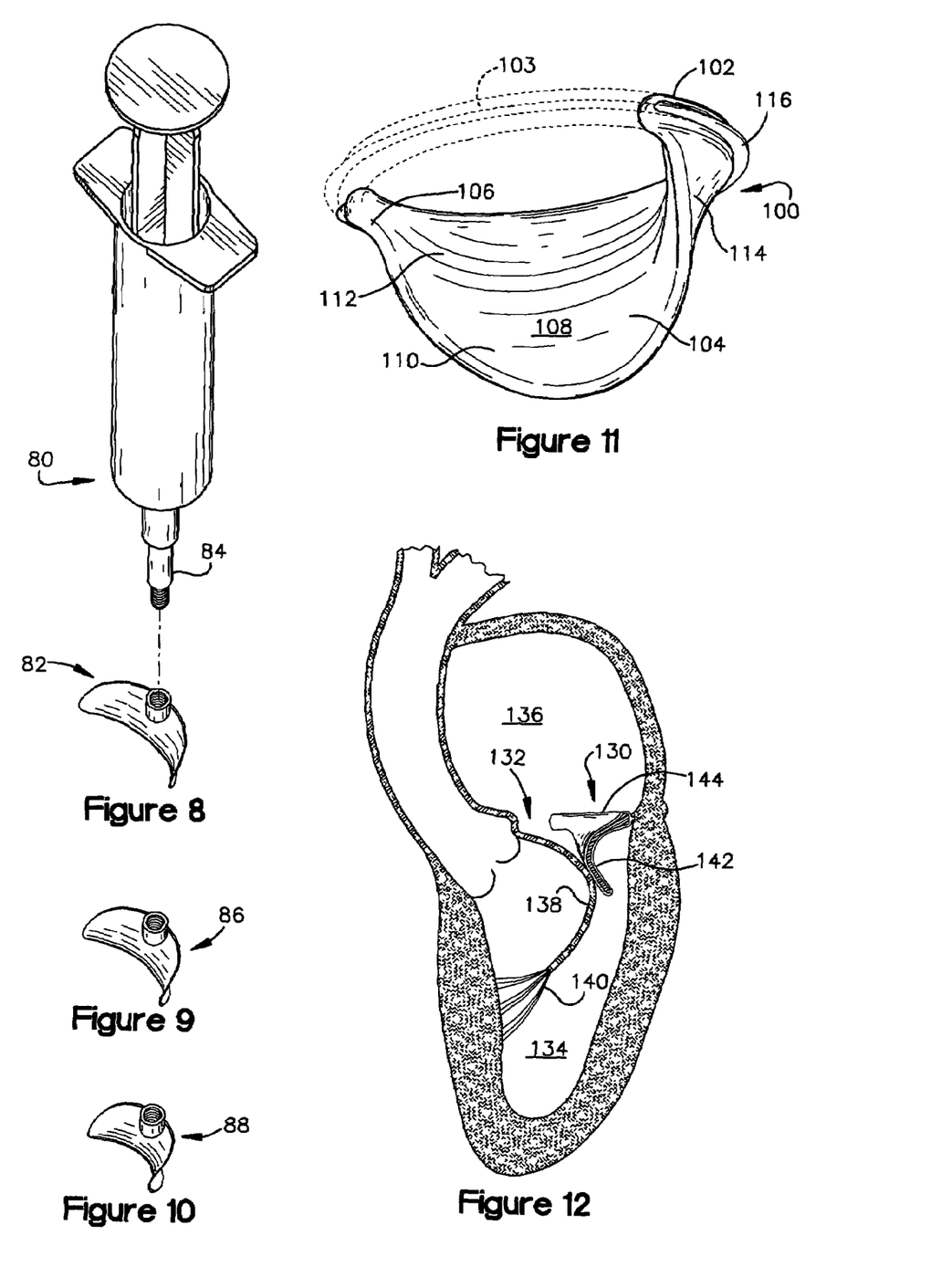
FIG. 8 is an assembly view of an apparatus in accordance with an aspect of the present invention with a contact member detached from the elongated member.
FIG. 9 is an example of a contact member in accordance with an aspect of the present invention.
FIG. 10 is another example of a contact member in accordance with an aspect of the present invention.
FIG. 11 is an isometric view of a cardiac prosthesis that can be employed in accordance with an aspect of the present invention.
FIG. 12 is a cross-sectional view of a part of a heart in which the cardiac prosthesis is implanted at a heart valve in accordance with an aspect of the present invention.

FIG. 8 illustrates an apparatus 80 is provided where a contact member 82 can be made selectively detachable from an elongated member 84 In accordance with an aspect of the present invention. The selective attachment allows a surgeon to select from a number of alternate contact members of different size if the original contact member 82 is too large or too small. By way of example, the distal end of the elongated member 84 can be threaded to allow a contact member to be screwed onto the elongated member. Those skilled in the art will appreciate other types of connections or fittings (e.g., friction fitting, snap fitting, clamps and the like) that can be utilized.

FIGS. 9 and 10 illustrate examples of alternative contact members, 86 and 88. With the new contact member, the surgeon can repeat the sizing procedure described above to better approximate the size of an appropriate prosthetic leaflet. A desired one of the contact members 82, 86, 88 can be attached to the elongated member by any of a number of means known in the art.

FIG. 11 illustrates an example of a cardiac prosthesis 100 that can be implanted according to the present method. For example, the prosthesis 100 can be of the type shown and described in U.S. patent application Ser. No. 10/215,800, filed on Aug. 4, 2002, to Gabbay, which is hereby incorporated by reference.

The prosthesis 100 includes a generally arcuate base portion 102 that can be closed or C-shaped. In accordance with an aspect of the present invention, a section of the base portion, indicated as a dotted portion 103, can be removable from the prosthesis 100 (e.g., by cutting) so that a surgeon can select the type of annulus desired—ring-like or C-shaped. The base portion 102 includes a support ring, which can be formed of a flexible, resilient, or generally rigid material. The support ring can have an elastic property that returns the ring to its original shape when deflected from its original (or rest) condition. The support ring, for example, can be a plastic-like material (e.g., a polymer, a resin, etc.) or a metal (e.g., stainless steel, a shape memory alloy, such as NITINOL), such as in the form of a wire. It will be understood and appreciated that other types of generally rigid, elastic, and/or resilient materials also can be used in accordance with the present invention. In addition, a suitable inelastically deformable material also could be used to form the support ring.

A buttress 104 extends generally axially from an outflow side 106 of the base portion 102. Briefly stated, a proximal portion 108 of the buttress 104 extends generally axially and radially inward from the base portion 102. A distally extending portion 110 of the buttress 104 extends from the proximal portion 108 and curves radially outwardly therefrom for the remaining length of the buttress. The buttress 104 has a radially inner surface 112 that provides a surface against which a leaflet (e.g., an anterior leaflet of a mitral valve) can coapt at valve closure.

The prosthesis 100, including the buttress 104, can be selected according to the dimensions and configuration of a contact member from a sizing apparatus that has been determined to provide desired coaptation. Consequently, when the prosthesis 100 is implanted within a heart valve, a leaflet (or leaflets) can engage the buttress 104 to close the valve and provide substantially unidirectional flow of blood therethrough. The leaflet (or leaflets) is able to coapt with the inner surface 112 of the buttress 104, thereby inhibiting regurgitation of blood when the ventricle contracts.

The prosthesis 100 can also include an outer sheath 114 of a flexible, biocompatible material covering the apparatus. The apparatus 100 also can include an implantation flange 116 (or sewing ring) that circumscribes the base portion 102 of the apparatus. The implantation flange 116 extends radially outwardly from the base portion 102 for facilitating implantation of the apparatus 100 at a heart valve. Each of the outer sheath 114 and the implantation flange 116 can be formed of any suitable flexible, biocompatible material, such as a clothlike or fabric (natural or synthetic) material or a biological material, such as collagen or an animal tissue material. An acceptable animal tissue material is smooth animal pericardium (e.g., equine, bovine, porcine, etc.), such as a NO-REACT® tissue product, which is available from Shelhigh, Inc. of Union, N.J.

Implantation of a cardiac prosthesis can be accomplished by several means. For the type of prosthesis illustrated in FIG. 11, these means will generally require open heart surgery. For example, the base portion 102 can be sewn to the wall of the valve 54 at the implantation flange 116 to hold the prosthesis in place. The base portion 102 can also include barbs or hooks (not shown) that extend radially from the exterior of the base potion, such as disclosed in the above incorporated Gabbay patent application. These barbs can be pressed into the wall of the valve to directly engage the muscle tissue of the valve.

The implantation of other types of prostheses can be less invasive. For example, a prosthesis can be designed to be reducible to a smaller cross-sectional dimension for placement via a catheter or a type of implantation. The sizing tool and process used for these non-invasive techniques can vary from those described above, in accordance with additional aspects of the present invention.

FIG. 12 illustrates a part of a heart in which a prosthesis 130 is implanted at a mitral valve 132. For the purpose of example, the implanted prosthesis will be the type of prosthesis 100 illustrated in FIG. 11, but in which the removable section 103 of the annular base 102 has been removed. It will be appreciated, however, that the present invention is not limited to use with this prosthesis. A number of other cardiac prostheses are available and suitable for use with the sizing apparatus of the present invention.

The valve 132 facilitates a unidirectional flow of blood from the left atrium 134 into the left ventricle 136. The mitral valve 132 includes an anterior leaflet 138 that extends from the valve opening and attaches to muscular tissue in the wall of the left ventricle by fibrous cordae tendinae 140. A posterior leaflet (not shown) extends from an opposing surface of the valve opening and coapts the anterior leaflet at valve closure. In FIG. 12, the posterior leaflet has been substantially removed from the heart, such as by excising it before implanting the prosthesis 130. It is to be understood and appreciated, however, that the posterior leaflet can remain intact, with a buttress 142 of the prosthesis 130 interposed between the posterior and anterior leaflets.

The buttress 142 extends from a base 144 of the prosthesis 130 into the ventricle 136 at a position corresponding to the position of the posterior leaflet of the mitral valve 132. As mentioned above, the buttress 142 extends into the ventricle 136. It is to be appreciated that the buttress 142 can be formed of a generally rigid material that remains substantially stationary (e.g., static) during both the open and closed positions of the valve. Alternatively, the buttress 142 can be a sufficiently flexible material to permit movement thereof commensurate with the flow of blood from the atrium 136 into the ventricle 136 through the valve 132.

FIG. 12 illustrates the anterior leaflet 138 engaging the buttress 142 of the prosthesis 130, operating as a closed valve. In this way, the buttress 142 of the prosthesis 130 simulates the function of the posterior leaflet at valve closure by providing a surface against which the anterior leaflet 138 coapts. Consequently, the buttress 142 and the anterior leaflet 138 cooperate to inhibit regurgitation of blood from the left ventricle 136 into the left atrium 136, such as during ventricular contraction.

The buttress 142, in conjunction with the anterior leaflet 138, facilitates and promotes unidirectional flow of blood when the valve is open. In particular, when a prosthesis 130 of an appropriate size is implanted, an opening or aperture extends through the implanted prosthesis 130 between the buttress 142 and the anterior leaflet 138. Advantageously, the movement of the anterior leaflet 138 relative to the buttress 142, in response to the flow of blood during the contraction of the left atrium 136, provides a sufficient orifice to permit the substantially free flow of blood from the left atrium into the left ventricle 136. The buttress 142 also can be formed of a flexible material that is able to move radially relative to the base portion 144 to further facilitate blood flow.

Figure 13:
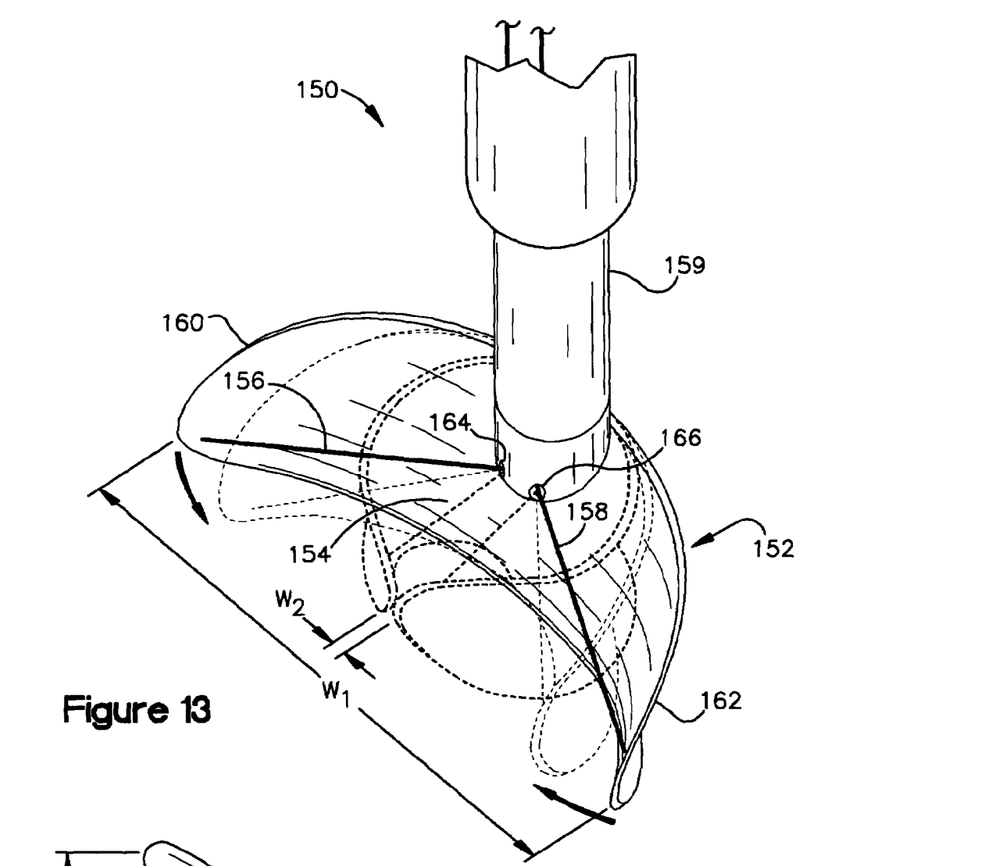
FIG. 13 is an elevated side view of a sizing apparatus in accordance with another aspect of the present invention.

FIG. 13 illustrates an apparatus 150 in accordance with another aspect of the invention. The apparatus 150 includes a contact member 152. As is illustrated in FIG. 13, the contact member 152 can be capable of assuming multiple configurations having different associated cross-sectional dimensions. The contact member has a curved surface 154 with an associated shape and area varying with the configuration of the contact member 152. In the example of FIG. 13, the cross-sectional width dimension is shown to vary between W1 and W2, where W1>W2. In this way, a given apparatus can accommodate differently sized valves. Additionally, the positioning of the by contact member at the patient's heart valve can be facilitated when the contact member is at a reduced cross-section. In at least one configuration of the contact member 152, the curved surface 154 is shaped to engage a leaflet within a heart valve.

The contact member 152 can be made from a material having with a natural shape and a tendency to return to that natural shape in the absence of a deforming force and the capacity to be deformed from that natural shape by pressure or some other means. By way of example, the contact member can be formed from a shape memory alloy material, such as Nitinol. Such an alloy can be formed into a particular shape and treated to allow it to "remember" that form. At low temperatures, the material remains pliant, but at higher temperatures, such as those within a patient's body, the material will attempt to revert to the remembered form. The shape memory alloy can be coated with natural or synthetic material, such as a soft plastic, rubber or biological material (e.g., animal pericardium, dura matter, etc.).

For example, the natural shape of the material corresponds to the configuration of the contact member having the largest cross-sectional dimension W1. It will be appreciated, however, that the apparatus may be designed such that the natural shape is the configuration with the smallest cross-sectional dimension W2 or an intermediate cross-sectional dimension, depending on the requirements of a given application.

The illustrated contact member 152 can be deformed into a configuration having a smaller cross-sectional dimension (e.g., less than W1) by one or more control members. In the illustrated embodiment, the control members include one or more elongated restraints 156 and 158, such as sutures. It will be appreciated that the one or more control members of the device may take a number of forms, and that the illustrated device is merely exemplary.

The restraints are connected at their distal ends to the lateral edges 160 and 162 of the contact member 152 to hold the contact member in a configuration having a reduced cross-sectional dimension. An elongated member 159 extends from the contact member 152 to a proximal end (not shown). One or more apertures (also not shown) extend through the elongated member 159 from its proximal end 162 to a point near the contact surface 154 of the contact member 152. The restraints 156 and 158 extend through one or more orifices 164 and 166 into the aperture within the elongated member 159 at a point near the contact surface 154. The restraints 156 and 158 extend through the aperture to a proximal end 162 of the elongated member 160. At the proximal end, the restraints 156 and 158 can be fastened by their proximal ends to a control device (not shown) to maintain a necessary tension within the restraints 156 and 158 to deform the contact member 152.

The configuration of the contact member 152 can be controlled by the control device at the proximal end of the elongated member 159. The control device is operative to increase or decrease the length of the restraints 156 and 158 between the proximal end 162 of the elongated member 159 and the lateral edges 160 and 162 of the contact member 152. As the portion of the restraints 156 and 158 between the proximal end 162 and the lateral edges 160 and 162 of the contact member 152 is shortened, the restraints operate to pull the lateral edges closer together, reducing the cross-sectional dimension of the contact member (e.g., to less than W1). When the tension on the restraints 156 and 158 is loosened, such as to increase the length of the restraints between the apertures 164 and 166 and the respective lateral edges 160 and 162, the lateral edges will move apart as the contact member 152 attempting to return to its natural configuration (e.g., W1). The expanded size thus will vary according to the length of the restraints between the apertures 164 and 166 and the respective lateral edges 160 and 162.

It will be appreciated that the control device can include any of a number of devices useful in controlling the tension on the restraints 156 and 158. For example, one or more wheels can gather a portion of the restraints 156 and 158 into a coil under manual or mechanical pressure. Alternatively, one or more restraining clips on the exterior of the device can be employed to enable the user to withdraw or release a portion of the restraints manually and clip the restraints into place at a desired length. Similar examples should be apparent to one skilled in the art in light of the foregoing discussion.

Regardless of the specific control device used, markings or indicia can be provided on the device, for example, on the device exterior, to directly or indirectly measure the length of the restraints 156 and 158 between the proximal end 162 and the lateral edges 160 and 162 of the contact member 152. The apparatus 150 can be calibrated such that a particular length of one or more of the restraints 156 and 158 will correspond to a cross-sectional dimension of the contact member 152, allowing the cross-sectional dimension to be determined from the measurement of the length of the one or more restraints.

An intended purpose of the apparatus 150 of FIG. 13 is its use in a minimally invasive sizing process to precede implantation of a valvuloplasty device, such as shown and described in the above-incorporated Gabbay patent application. The illustrated contact member 152 can be deformed to a configuration having a reduced cross-sectional dimension to facilitate placement of the device. The apparatus 150 can be mounted to a catheter, an elongated handle, or another positioning device for insertion into a heart valve. An appropriate vision system can be included with the apparatus 150 to guide the placement of the apparatus 150 and determine if a particular configuration of the contact member provides effective coaptation with any viable leaflets in the valve.

Where the apparatus 150 is mounted to an elongated handle, a low invasive minithoracotomy can be used to gain access to the heart of the patient and the apparatus 150 can be inserted through the minithoracotomy passage. The contact member 152 is first placed into a configuration having a minimal cross-sectional dimension. The surgeon can then guide the apparatus 150 through the passage using an appropriate vision system to bring the contact member 152 into a desired position for engaging with any viable leaflets of the valve. The cross-sectional dimension of the contact member can then be expanded to the size where it engages with the viable leaflets and the cross-sectional dimension necessary to provide effective coaptation can be recorded. The point where effective coaptation takes place can be determined by the surgeon using the vision system. The cross-sectional dimension of the contact member 152 can then be reduced back to its initial, minimal configuration to facilitate withdrawal of the device. It will be appreciated that such a procedure can be implemented with little or no cardiopulmonary bypass.

Similarly, where the apparatus 150 is mounted to a catheter, it can be inserted into the heart valve from a remote entry point within the body. When a catheter is used to position the apparatus 150, an electromechanical mechanism can be used to adjust the length of the restraints 156 and 158 and accordingly, adjust the configuration of the contact member 152, as the restraints 156 and 158 may not be in a position to be manually adjusted. The cross-sectional dimension of the contact member 152 can be reduced to facilitate passage through blood vessels into the valve, and expanded to measure the size of a prosthetic replacement necessary to provide effective coaptation of any viable leaflets. The cross-sectional dimension of the contact member 152 can then be reduced to allow the apparatus 150 to be removed.

Figure 14:
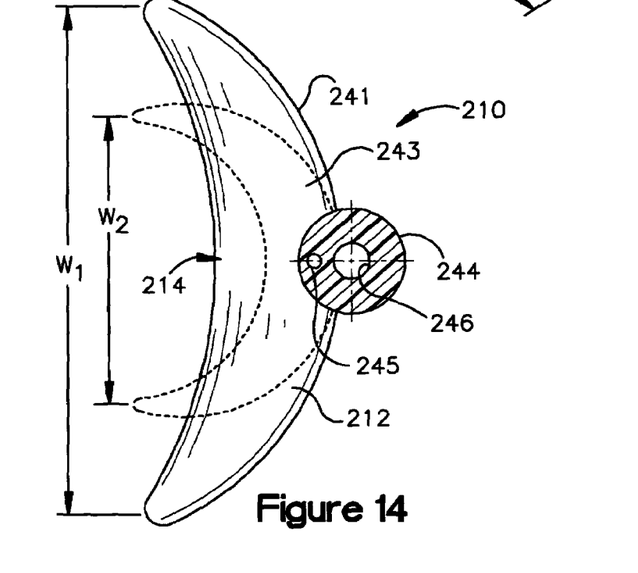
FIG. 14 is an overhead view of a sizing apparatus in accordance with yet another aspect of the present invention.

FIG. 14 illustrates an apparatus 210 in accordance with another aspect of the invention. The apparatus 210 includes a contact member 212. As is illustrated in FIG. 14, the contact member 212 is capable of assuming a plurality (e.g., at least two) configurations, each having a different associated cross-sectional dimension. Two such dimensions are depicted at W1 and W2, where W1>W2. The contact member 212 has a curved surface 214 with an associated shape and area varying with the configuration of the contact member 212. The size contact member 212 thus is variable to accommodate differently sized heart valves. Additionally, the contact member can be provided in a sufficiently reduce cross-sectional dimension to facilitate its positioning at a patient's heart valve by minimally invasive means according to an aspect of the present invention.

The contact member 212 (or at least the surface 214 thereof) is formed from a fluid impermeable membrane 241 defining an interior chamber. The outer membrane 241 can be formed from rubber, flexible plastic, or any other elastic, fluid-impermeable substance that is substantially biocompatible. The interior chamber of the member 212 is connected to a fluid source (not shown) that can be located near the proximal end of the elongated member 244 through a conduit 245 or other fluid communicating member. The conduit 245, for example, can be formed as an aperture extending through the elongated member 244.

A control device (not shown) on the fluid source directs a fluid through the aperture 245 to the interior chamber. This mechanism can be a pump, a syringe, a bellows, or any similar device for encouraging the flow of fluid. The fluid itself may be air, water, saline, blood, or any other biocompatible fluid. As the interior chamber fills with fluid, it inflates the outer membrane 241 causing the contact member 212 to assume a configuration having a cross-sectional dimension functionally related to the amount of fluid in the chamber of the member 212. The cross-sectional dimension of the contact member 212 can be ascertained according to the amount of fluid that is directed into the interior chamber. The apparatus 210 can be calibrated such that a particular fluid level can be translated into an appropriate cross-sectional dimension. A control device can include means for evacuating the fluid within the interior chamber, either back into the fluid source, or into the heart valve.

An intended purpose of the apparatus 210 illustrated in FIG. 14 is its use in a minimally invasive sizing process to precede implantation of a valvuloplasty device. In this process, the contact member 212 begins with the outer membrane 241 deflated to provide a reduced cross-sectional dimension that facilitates placement of the device. The apparatus 210 can be mounted to a catheter, an elongated handle, or another positioning device for insertion into a heart valve. The fluid source can connect to the contact member 212 through an aperture 246 in the elongated member 244. An appropriate vision system can be included with the device to guide the placement of the device and determine if a particular configuration of the contact member 212 provides effective coaptation with any viable leaflets in the valve.

Where the apparatus 210 is mounted to an elongated handle, a low invasive minithoracotomy can be used to gain access to the heart of the patient, such that the apparatus 210 can be inserted through the minithoracotomy passage. The contact member 212 is placed in a deflated configuration having a minimal cross-sectional dimension to facilitate positioning of the device. The surgeon can then guide the apparatus 210 through the passage using an appropriate vision system to place the contact member 212 at a desired position for engaging one or more viable leaflets of the valve. The cross-sectional dimension of the contact member 212 can then be selectively expanded through inflation of the outer membrane 241 to the point where the viable leaflets can engage the surface 214 to inhibit flow of fluid through the valve annulus (e.g., simulating operation of competent heart valve). The cross-sectional dimension necessary to provide effective coaptation can be recorded based on the amount of fluid provided to the inner chamber, for example. The coaptation between the contact member and the valve leaflet (or leaflets) can be determined by the surgeon using the vision system. The cross-sectional dimension of the contact member 212 can then be reduced back to its initial, minimal configuration to facilitate withdrawal of the device by evacuating the fluid within the device. It will be appreciated that such a procedure can be implemented with little or no cardiopulmonary bypass.

Similarly, the apparatus 210 can be mounted to a catheter for insertion into the heart valve from a remote entry point of the body. When a catheter is used to position the apparatus 210, a separate tube can be included to carry fluid to the interior chamber from the fluid source to adjust the configuration of the contact member 212. The cross-sectional dimension of the contact member 212 is placed in a reduced form to facilitate passage through blood vessels into the valve. The inner chamber of the contact member 212 is then filled at least partially with fluid to expand the contact member 212 to determine a suitable size of a prosthetic device to provide effective coaptation of any viable leaflets. The cross-sectional dimension of the contact member 212 can then be reduced to allow the apparatus 210 to be removed by evacuating the fluid from the inner chamber.

Figure 15:
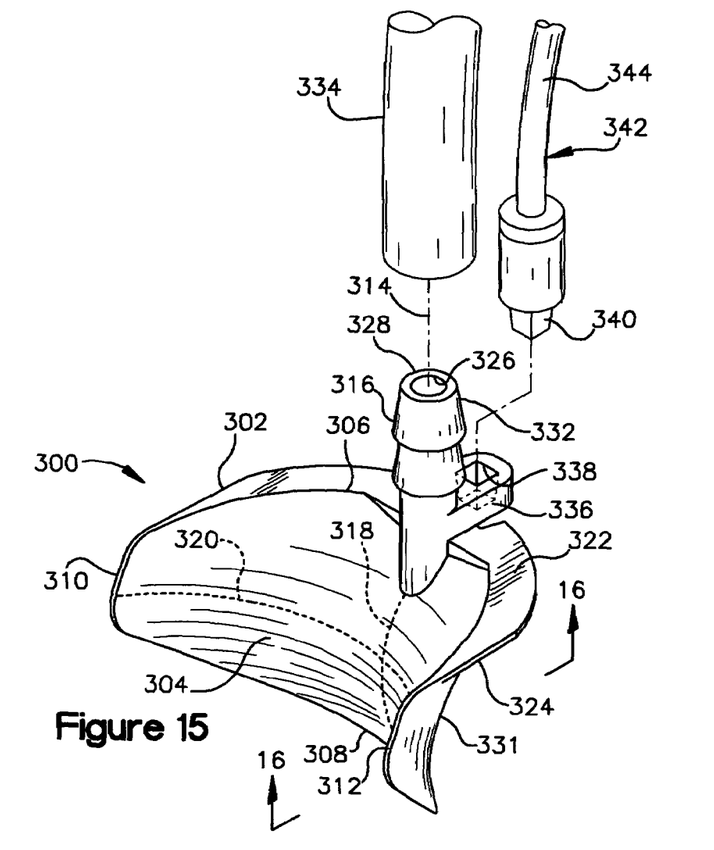
FIG. 15 is a perspective view of a sizer apparatus in accordance with yet another aspect of the present invention.
Figure 16:
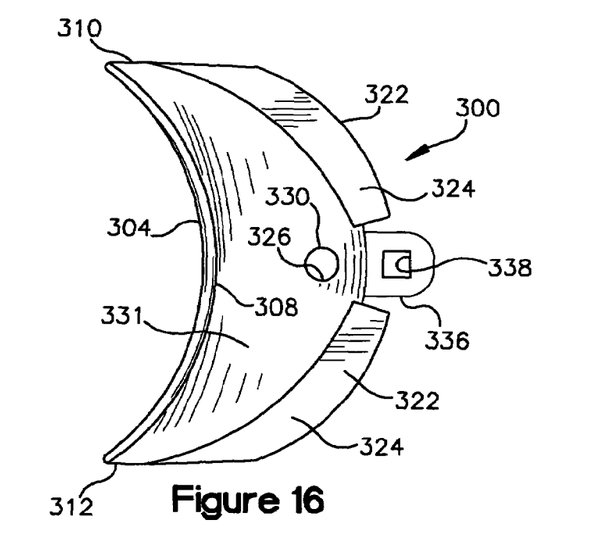
FIG. 16 is a bottom view of the sizer apparatus taken along line 16-16 of FIG. 15.

FIGS. 15 and 16 depict an example of another sizer apparatus 300 according to an aspect of the present invention. The sizer apparatus 300, similar to the other sizer apparatuses shown and described herein, includes a contact member 302 having a curved contact surface 304. The contact surface 304 includes an inflow (or proximal) end 306 spaced apart from a distal end 308 by spaced apart side edges 310 and 312 that extend between the inflow end and the distal end. As shown in FIG. 15, the contact surface 304 extends in a substantially convex shape from the proximal end 306 to the distal end 308 along a direction (indicated at curved dotted line 318) that lines in the same plane as an axis 314. The axis 314, for example, corresponds to a central longitudinal axis that extends through or is at least parallel with an arm 316 that extends from the contact member 302. The contact surface 304 also extends in a substantially concave shape between spaced apart side edges 310 and 312 along a direction (indicated at curved dotted line 320) that lines in a plane that is substantially transverse to the first axis 314. Thus, the contact surface 304 can be dimensioned and configured to simulate the dimensions and configuration of a coaptating surface of a heart valve leaflet at its closed position.

With the axis 314 as a reference, the dimension along the line 318 can be considered an axial dimension and the dimension along the line 320 can be considered a transverse or lateral dimension of the contact member 302. In the example of FIG. 15, the length of the surface 304 in the transverse dimension (e.g., between the side edges 310 and 312 along the dotted line 320) is greater than the length of the surface 304 along the axial dimension (e.g., between the proximal and distal ends 306 and 308 along the dotted line 318). The portion of the curved surface 304 between the axial line 318 and the side edge 310 further can be substantially symmetrical relative to the portion of the curved surface between the axial line 318 and the side edge 312. The transverse dimension as well as the direct or linear distance between the side edges 310 and 312 can vary to accommodate different size patients (including humans and other animals) as well for treatment in different types of heart valves (bicuspid and tricuspid valves). For example, a range of different sized apparatuses 300 can be available, such having diameters (e.g., the direct distance between side edges 310 and 312) ranging between about 15 mm and about 50 mm. Different transverse dimensions can also be provided for use in simulating different types and sizes of valve leaflets.

The sizing apparatus 300 further can include a flange 322 that extends outwardly from at least a portion of the proximal end 306 of the curved surface 304 of the contact member 302. As depicted in FIGS. 15-16, the flange 322 extends outwardly from the contact member 302 to define a shoulder along an underside surface 324 of the flange that is opposite the contact surface 304. The juncture between the curved surface 304 and the flange 322 can define at least a portion of the proximal end 306. The flange can be substantially flat or it may be curved. As one example, the flange 322 can be substantially flat, such that the surface 324 lies in a plane that is substantially perpendicular to the axis 314. The flange 322 can also extend from the contact member as two or more bifurcated sections, such as depicted in FIGS. 15-16, or it can be implemented as a continuous extension along the proximal end 306 of the contact member 302. As described herein, the shoulder surface 324 can be positioned to engage the annulus of a heart valve to facilitate positioning the sizing apparatus 300.

The arm 316 extends outwardly from the curved surface 304 at a location that is adjacent the proximal end 306 of the curved surface. The arm 316 can be located intermediate the first and second side edges 310 and 312, such as spaced substantially equidistance between the side edges (e.g., aligned with the axially extending center line 318). As shown in FIG. 15, the arm 316 can be a tubular structure that includes an aperture 326 extending from a proximal end 328 substantially axially through the arm 316 and terminating in an opening 330 adjacent a surface 331 of the contact member 302 that is opposite the contact surface 304. The aperture 326 provides for fluid communication through the contact member 302, such as can be utilized to urge one or more existing leaflets of a patient's heart valve into the contact surface 304.

The arm 316 further can be configured to include one or more retaining features 332 along an exterior surface of the arm. The retaining features 332, for example, can be configured as one or more axially displaced frusto-conical sidewall fittings, such that a substantially flexible conduit (or tube) 334 can be urged axially onto the retaining features. Other means for attaching the tube 334 to the arm 316 can be used, such as threads, pins, latches, clamps and the like. The conduit 334, for example, can be connected with a fluid source to supply fluid into the aperture 326, such as described herein.

The apparatus 300 can also include a support tab 336 that extends outwardly from the arm 316. For example, the tab 336 can extend along a plane that is substantially parallel to proximal surface of the flange 322 and generally transverse to the axis 314. A slot 338 can extend through at least a portion of the support tab 336 spaced apart from the arm 316. The slot 338 can correspond to a receptacle into which a mating plug 340 can be positioned. The plug 340 can form a distal end of a holder 342 for the apparatus 300. An elongated shaft 344 can extend from the plug 340 to form an elongated handle of such holder 342 that can be attached to the apparatus 300. The holder 342 thus can be utilized to place the apparatus to a desired position in a patient's heart (e.g., at an inflow annulus of a heart valve). Those skilled in the art will understand and appreciate that various means of attaching the holder 342 to the apparatus can be utilized, including demountable friction fittings, snap fittings, adhesives, threads, welding (ultrasonic or otherwise depending on materials being used). Alternatively, the handle 342 can be integrated as part of the apparatus 300.

The apparatus 300 can be fabricated from one or more substantially rigid, durable material that is substantially biocompatible, such as described herein. For instance, the flange, the contact member and the arm can be integrally formed of the same material by appropriate processes according to the type of material being used (e.g., by molding, stamping, casting, extrusion, machining, or other manufacturing techniques). Alternatively, different materials could be used for different parts of the apparatus 300.

FIGS. 17, 18, 19 and 20 depict an example of the sizer apparatus 300 positioned at an annulus 350 heart valve 352 according to an aspect of the present invention. Solely for the purpose of example, the valve 352 is illustrated in FIGS. 17-20 as a mitral valve within a human heart, and the method is discussed in the context of evaluating the valve 352. As an example, the apparatus 300 can be utilized to determine the extent of a repair procedure, which might include implanting a cardiac prosthesis, such as of the type shown and described with respect to FIG. 11. One skilled in the art will appreciate, however, that the apparatus of the present invention may be used in other valves within the human heart, such as the tricuspid, pulmonary, or aortic valves, as well as in valves within animal hearts. Likewise, the present invention may be used to size a replacement for any leaflet, including the anterior leaflet of the mitral valve or the leaflets of any of the aforementioned valves. Additionally, the apparatus 300 can be utilized in conjunction with other heart valve repair procedures, to evaluate the extent of repairs needed as well as to ascertain whether the valve should be repaired or replaced. These and other uses are intended to be encompassed by the apparatuses and methods described herein.

Figure 17:
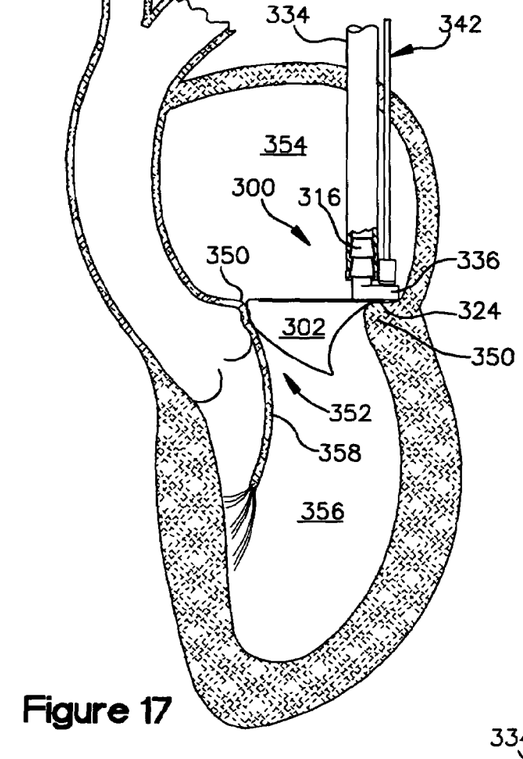
FIG. 17 is a cross-sectional view of the apparatus of FIG. 16 positioned within the heart valve of a patient, illustrating a first condition of the heart valve.
Figure 18:
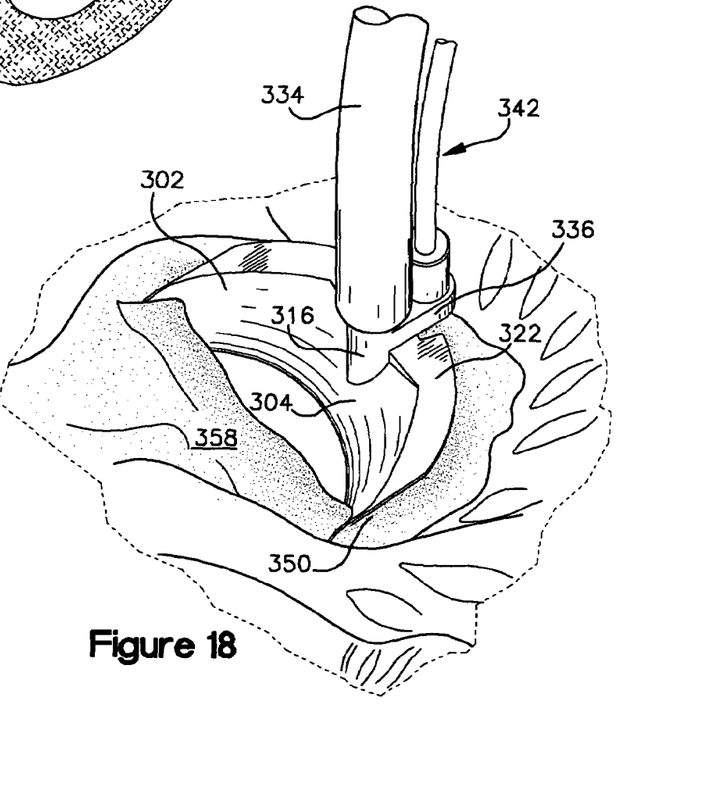
FIG. 18 is an inflow view of the apparatus and heart valve of FIG. 17.

In the example of FIG. 17, the mitral valve 352 is located between the left atrium 354 and the left ventricle 356. The anterior leaflet 358 of the patient's valve 352 is present and viable, but the posterior leaflet (not shown) is either nonviable or has been surgically removed. By way of example, the sizing apparatus 300 is positioned at the annulus 350 of the valve 352 so that the curved contact surface 304 of the contact member 302 faces the anterior leaflet 358, essentially simulating the configuration of the posterior leaflet in a closed position. For instance, the flange 322 is positioned with its lower surface 324 engaging the inflow annulus 350 approximating the periphery between the side edges of the anterior leaflet (corresponding to periphery of the posterior leaflet). In accordance with one aspect of the present invention, the apparatus 300 can be positioned manually by a user holding an elongated handle of the holder 342, which is attached to the tab 336 that extends radially outwardly from the arm 316. Those skilled in the art will understand and appreciate that other elongated structures can be attached (removably or permanently) for positioning apparatus 300 at the annulus 350. FIG. 18 depicts an inflow view of the sizing apparatus 300 when the valve 352 is in the open position.

Figures 19, 20:
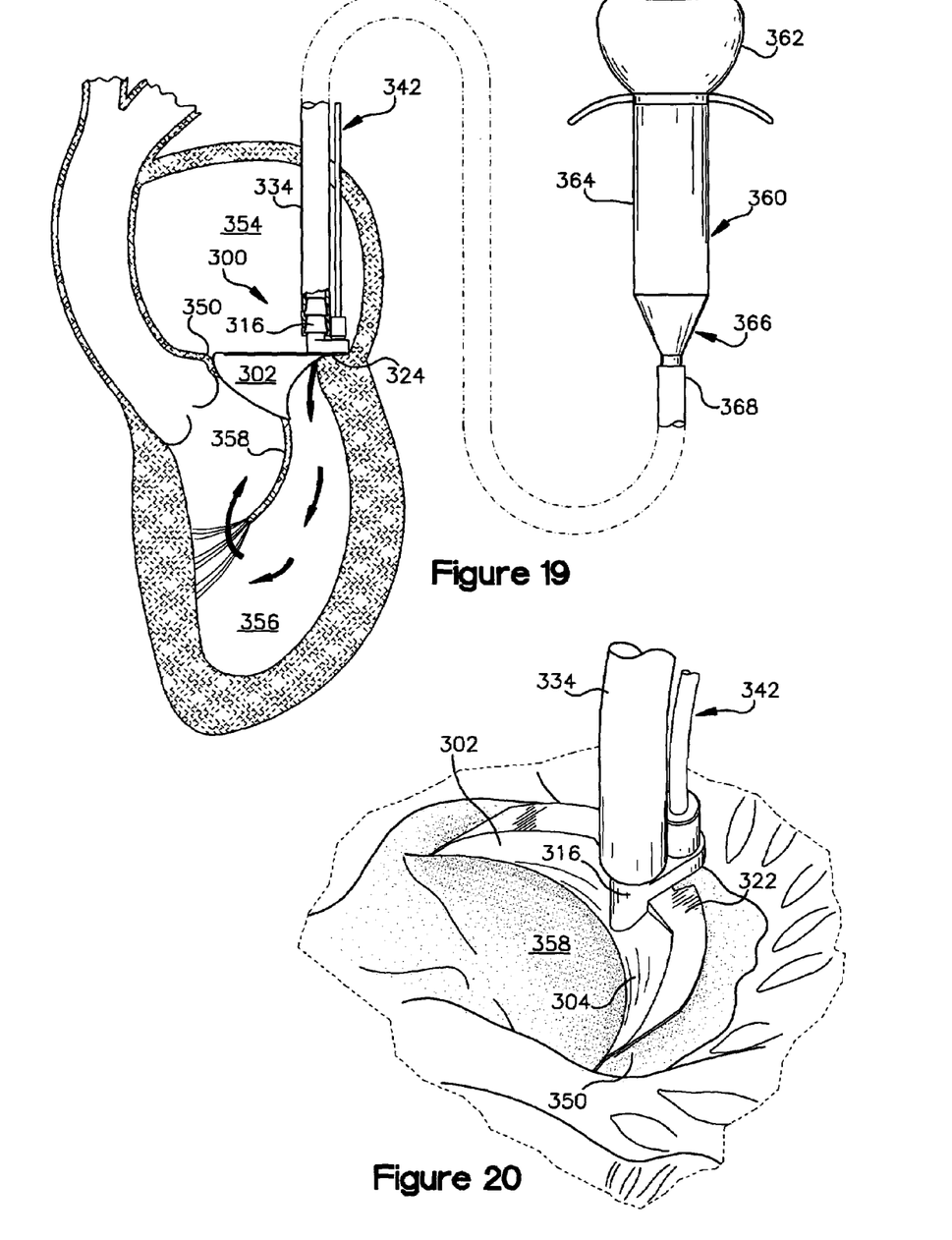
FIG. 19 is a cross-sectional view of the apparatus of FIG. 16 positioned within the heart valve of a patient, illustrating a second condition of the heart valve.
FIG. 20 is an inflow view of the apparatus and heart valve of FIG. 19.

To better ascertain the type and extent of valve repair required, including the appropriate size of a cardiac prosthesis, a user can supply fluid into the ventricle 356 for urging the leaflet 358 into engagement with the contact surface 304 of the contact member 302. By way of example, referring to FIGS. 19 and 20, the user can supply fluid through the contact member 302. For instance, a flexible tube 334 can connect the arm 316 with a source of fluid 360. In the example of FIG. 19, the fluid source 360 includes a hand pump having a compliant bulb 362 connected with a proximal end of an elongated cylindrical body 364. A distal end (e.g., having a conical cross-section) 366 of the body 364 tapers to a dimension for receiving a proximal end 368 of the flexible tube 334. As described herein, fluid thus flows from the cylindrical body 364 into the tube 334, through an aperture 326 (see FIG. 15) in the apparatus 300 and into the left ventricle 356. As discussed previously, various means for supplying fluid into the ventricle 356 can be used, such as including a pump, syringe, or a stopcock to name a few. The fluid injected into the ventricle 356 (as represented by the series of arrows) urges the anterior leaflet 358 toward its closed position and toward the contact member the contact surface 304 of the contact member 302. Assuming that the apparatus 300 is an appropriate size, the anterior leaflet 358 can engage (or coapt) with the curved surface 304 to close the valve, as illustrated in FIGS. 19 and 20.

Once the anterior leaflet 358 has been urged into a closed position, the surgeon can examine the engagement between the anterior leaflet 358 and the contact member 302. Where the leaflet 358 and the contact member 302 coapt, as to substantially prevent the flow of fluid through from the valve (e.g., little or no regurgitation), a size of a corresponding cardiac prosthesis can be determined according to the size of the contact member 302. When the leaflet 358 and the contact member 302 properly coapt, the surgeon will know that a prosthetic device matching the size and shape of the contact member 302 is appropriate for implantation. Thus, different sized and shaped contact members can be used so as to determine an appropriately sized and shaped device.

Where there is not sufficient coaptation between the leaflet 358 and the contact member 358, a differently sized prosthesis should be used. For example, where the contact member 302 is too small to effectively coapt the leaflet 358, the surgeon may see small spaces or gaps between the leaflet 358 and the contact member 302. This indicates a larger size prosthesis may be needed. This can be confirmed by repeating the sizing process with a larger sized contact member.

Where the contact member 302 is too large, the annulus of the valve 352 may distort, thereby preventing desired coaptation between the contact member 302 and the leaflet. Additionally or alternatively, the orifice between the contact member 302 and the leaflet may be considered be too small. A surgeon thus can readily ascertain that a prosthetic device matching the size of the contact member would be too large and seek a smaller device. By injecting fluid, a user can also determine if it may be desirable to utilize an oversized cardiac prosthesis as well as conclude whether other types of valve repair may also be desirable.

In view of the foregoing, an apparatus according to the present invention provides a useful apparatus for determining the proper size of a valvuloplasty device intended for implantation into a heart valve. The sizer apparatus can also be utilized during other heart valve repair procedures or to ascertain whether repair is a suitable option as well as the extent and type of repair that may be needed, or whether valve replacement would be a preferred option. Various embodiments of the apparatus that are useful for a minimally invasive sizing procedure have been provided. Accordingly, it is be understood that the various features disclosed in FIGS. 1-20 can be combined in various ways according to an aspect of the present invention.

What have been described above are examples of the present invention. It is, of course, not possible to describe every conceivable combination of components or methodologies for purposes of describing the present invention, but one of ordinary skill in the art will recognize that many further combinations and permutations of the present invention are possible. For example, while many of the illustrated examples show the discuss the treatment of a bicuspid (mitral) valve, an apparatus in accordance with the present invention can also be useful in sizing prosthetic devices for other types of heart valves (e.g., a tricuspid valve or other bicuspid valves). Additionally, the sizer apparatuses shown and described herein can also be utilized in conjunction with other types of valve repair. Accordingly, the present invention is intended to embrace all such alterations, modifications and variations that fall within the spirit and scope of the appended claims.

What is claimed is:

1. A sizer apparatus, comprising:
    a contact member having a curved and continuous contact surface, the contact surface extending in a substantially convex shape from a proximal end to a distal end along a first direction that lies in a same plane as a first axis, the contact surface extending in a substantially concave shape between spaced apart first and second side edges along a second direction that lies in a plane that is substantially transverse to the first axis, the first direction and the second direction being substantially traverse to each other;
    an arm extending from the contact member substantially parallel to the first axis; and
    an aperture extending substantially axially through the arm and terminating in an opening adjacent a surface of the contact member opposite the contact surface to provide for fluid communication through the contact member.

2. The apparatus of claim 1, further comprising a fluid source operatively connected with a proximal end of the arm to supply fluid into the aperture.

3. The apparatus of claim 1, wherein the arm further comprises at least one retaining feature along an exterior surface near a proximal end of the arm.

4. A sizer apparatus, comprising:
    a contact member having a curved and continuous contact surface, the contact surface extending in a substantially convex shape from a proximal end to a distal end along a first direction that lies in a same plane as a first axis, the contact surface extending in a substantially concave shape between spaced apart first and second side edges along a second direction that lies in a plane that is substantially transverse to the first axis, the first direction and the second direction being substantially traverse to each other;
    an arm extending from the contact member substantially parallel to the first axis;
    a flange extending outwardly from at least a portion of the proximal end of the contact member;
    a support tab that extends radially outwardly from the arm to terminate in a tab end portion; and
    a slot extending through at least a portion of the support tab spaced apart from the first axis.

5. A sizing apparatus comprising:
    a contact member having a curved contact surface, the contact surface extending in a substantially convex cross-sectional shape from a proximal end to a distal end along a first direction that lies in the same plane as a first axis, the contact surface extending in a substantially concave cross-sectional shape between spaced apart first and second side edges along a second direction that lies in a plane that is substantially transverse to the first direction; and
    a flange extending outwardly from at least a portion of the proximal end of the contact member to define a shoulder along a surface of the flange that is opposite the contact surface of the contact member; and
    an arm extending from the contact member substantially parallel with the first axis and terminating in a proximal end spaced apart from the curved surface;
    wherein the arm extends from the curved surface of the contact member, the arm further comprising an aperture extending substantially axially through the arm from the proximal end and terminating in an opening adjacent a surface of the contact member opposite the contact surface to provide for fluid communication through the contact member.

6. The apparatus of claim 5, further comprising a fluid source operatively connected with the arm to supply fluid into the aperture.

7. A sizing apparatus comprising:

a curved surface having an inflow end spaced apart from a distal end by spaced apart side edges that extend between the inflow end and the distal end, the curved surface being dimensioned and configured to simulate the dimensions and configuration of a coaptating surface of a heart valve leaflet at systole in closed position; and a flange extending outwardly from at least a portion of the inflow end of the curved surface; and an arm extending from the curved surface at a location that is proximal the inflow end of the curved surface.

8. The apparatus of claim 7, wherein the curved surface extends in a substantially convex shape from the inflow end to the distal end along a direction that lies in the same plane as a first axis, the contact surface extending in a substantially concave shape between the spaced apart side edges along a direction that lies in a plane that is substantially transverse to the first axis, the arm extending substantially parallel to the first axis.

* * * * *